(12) United States Patent
Spinella et al.

(10) Patent No.: US 9,766,169 B2
(45) Date of Patent: Sep. 19, 2017

(54) PEELING APPARATUS AND METHOD FOR SEPARATING WELDED LAYERS

(71) Applicant: Arconic Inc., Pittsburgh, PA (US)

(72) Inventors: Donald J. Spinella, Greensburg, PA (US); Justin K. Williams, Indiana, PA (US); Robert J. Speer, Lower Burrell, PA (US); Sean Kelly, Pittsburgh, PA (US); Richard S. Dulski, Cheswick, PA (US)

(73) Assignee: Arconic Inc., Pittsburgh, PA (US)

( * ) Notice: Subject to any disclaimer, the term of this patent is extended or adjusted under 35 U.S.C. 154(b) by 139 days.

(21) Appl. No.: 14/713,210

(22) Filed: May 15, 2015

(65) Prior Publication Data
US 2015/0330884 A1     Nov. 19, 2015

Related U.S. Application Data

(60) Provisional application No. 61/994,181, filed on May 16, 2014.

(51) Int. Cl.
| | |
|---|---|
| *G01N 3/24* | (2006.01) |
| *G01N 3/08* | (2006.01) |
| *G01N 19/04* | (2006.01) |
| *G01N 21/88* | (2006.01) |

(Continued)

(52) U.S. Cl.
CPC ............... *G01N 3/08* (2013.01); *G01N 3/24* (2013.01); *G01N 19/04* (2013.01); *G01N 21/8806* (2013.01); *G01N 21/956* (2013.01); *G01N 25/72* (2013.01); *G01N 2203/0025* (2013.01); *G01N 2203/0091* (2013.01); *G01N 2203/0296* (2013.01)

(58) Field of Classification Search
CPC ... G01N 2203/0091; G01N 2203/0296; G01N 2203/0025; G01N 21/8806; G01N 21/956; G01N 25/72; G01N 3/08; G01N 3/24; G01N 19/04
USPC .......... 73/150 A, 150 R, 827, 829, 834, 842; 364/550, 558, 556, 570
See application file for complete search history.

(56) References Cited

U.S. PATENT DOCUMENTS

| | | | | |
|---|---|---|---|---|
| 2,989,865 | A * | 6/1961 | Belfour ................. | G01N 19/04 73/150 A |
| 3,524,345 | A * | 8/1970 | Isaacson ............... | G01N 19/04 73/150 A |

(Continued)

FOREIGN PATENT DOCUMENTS

DE          19856124          10/2009

OTHER PUBLICATIONS

International Search Report and Written Opinion of the International Searching Authority dated Aug. 19, 2015 in reference to International Application No. PCT/US15/30979.

*Primary Examiner* — Jonathan Dunlap
(74) *Attorney, Agent, or Firm* — Greenberg Traurig, LLP

(57) ABSTRACT

An apparatus and method for separating welded multi-layered samples has a slotted engine-driven spindle that twists and pulls a layer from the sample, breaking the welds as the layer winds around the spindle. The sample is held between two clamps and a tensioning cylinder pulls a movable first clamp against the second stationery clamp. Sensors may sense the force required to break the welds and the data may be stored and analyzed in a computer.

23 Claims, 5 Drawing Sheets

(51) Int. Cl.
  *G01N 21/956* (2006.01)
  *G01N 25/72* (2006.01)

(56) References Cited

U.S. PATENT DOCUMENTS

| | | | |
|---|---|---|---|
| 4,856,325 A * | 8/1989 | Tomita | G01N 19/04 702/43 |
| 4,893,503 A * | 1/1990 | Kimura | G01N 19/04 73/150 A |
| 5,275,489 A * | 1/1994 | Borneman | G01N 25/72 250/334 |
| 5,512,104 A | 4/1996 | Mizushiri et al. | |
| 5,566,570 A * | 10/1996 | Hankel | G01N 3/32 73/150 R |
| 5,602,341 A | 2/1997 | Lee et al. | |
| 6,185,999 B1 * | 2/2001 | Arrington | G01R 31/2805 73/150 A |
| 6,186,011 B1 | 2/2001 | Wung et al. | |
| 6,262,387 B1 * | 7/2001 | Chang | B23K 26/0823 219/121.63 |
| 6,478,264 B1 | 11/2002 | Nelson et al. | |
| 6,515,251 B1 | 2/2003 | Wind | |
| 6,813,958 B2 * | 11/2004 | Crosby | G01N 19/04 506/12 |
| 7,287,418 B2 * | 10/2007 | Yang | G01N 3/08 73/150 A |
| 7,913,552 B2 * | 3/2011 | Himmelbauer | G01N 19/04 73/150 A |
| 2005/0231713 A1 * | 10/2005 | Owen | G01N 21/8806 356/237.1 |
| 2007/0028432 A1 | 2/2007 | Evans et al. | |
| 2009/0114006 A1 * | 5/2009 | Himmelbauer | G01N 19/04 73/150 A |
| 2009/0128625 A1 * | 5/2009 | Loipetsberger | G01N 21/8806 348/90 |
| 2015/0317786 A1 * | 11/2015 | Huang | G06T 7/80 348/135 |

\* cited by examiner

PEELING APPARATUS AND METHOD FOR SEPARATING WELDED LAYERS

CROSS REFERENCE TO RELATED APPLICATIONS

This application claims the benefit of U.S. Provisional Application No. 61/994,181, filed May 16, 2014, entitled, Peeling Apparatus and Methods for Separating Welded Layers, which is incorporated by reference herein in its entirety for all purposes.

FIELD

The present invention relates to weld testing apparatus, and more particularly, to apparatus for destructive testing of welds.

BACKGROUND

Methods and apparatus are known for peel testing welded panels for quality assurance. These assessments is typically done through manual means which can vary in technique and efficiency from operator to operator. For example, AWS C1.1 illustrates peeling welded layers from one another using manually wielded pincers or a hammer and chisel. The results obtained are technique dependent and frequently produces separated panels that are highly distorted. In addition, manual methods may be both strenuous and slow. Alternative methods and apparatus for peel testing therefore remain desirable.

SUMMARY

The disclosed subject matter relates to a device for separating a first layer from a second layer conjoined to form a member. The device has: a base structure, a first clamp mounted on the base structure capable of retaining a first portion of the member including the first layer and the second layer therein, a second clamp mounted on the base structure at a distance from the first clamp approximating at least a portion of a length of the member and capable of retaining a second portion of the member including the first layer therein, a rotatable spindle having a slot therein capable of receiving a portion of the second layer at a position intermediate the first clamp and the second clamp and twisting the first layer around the spindle when the spindle is rotated and while the first layer is clamped by the first clamp and the second clamp to separate the second layer from the first layer.

In another embodiment, a member is coupled to the spindle and is capable of applying torque to the spindle.

In another embodiment, the member is a pulley.

In another embodiment, the pulley is a sprocket.

In another embodiment, the pulley is a gear.

In another embodiment, the member is a bar.

In another embodiment, the second clamp is movable and further includes a tensioner capable of applying tension to the member.

In another embodiment, the tensioner is hydraulically actuated.

In another embodiment, further including a slide and wherein the second clamp is mounted on the slide and capable of sliding on the slide in response to the application of tension by the tensioner.

In another embodiment, further including a spindle mount capable of rotatably supporting the spindle and a spindle slide capable of slidably supporting the spindle mount between a first position proximate the second clamp and a second position proximate the first clamp.

In another embodiment, further including an engine capable of turning the pulley.

In another embodiment, the pulley is a first pulley and further including a second pulley coupled to the engine and a drive connection extending between the first pulley and the second pulley, the first and second pulleys and drive connection providing a torque advantage for the engine to turn the spindle.

In another embodiment, further including a transducer capable of measuring energy expended in separating the second layer from the first layer of the member.

In another embodiment, further including a transducer capable of measuring tension experienced by the member as the second layer is separated from the member.

In another embodiment, further including a transducer capable of measuring force exerted by the spindle as the second layer is separated from the member for generating force data and a computer capable of receiving and storing the force data.

In another embodiment, further including a transducer capable of sensing a position of the spindle relative to the member and generating position data, the computer capable of correlating the force data and the position data.

In another embodiment, a method for separating a first layer from a second layer conjoined to form a member, includes: separating an end of the first layer from the second layer to form a separated end of the first layer and a separated end of the second layer; securing the separated end of the first layer of the member in a first clamp; securing the member at a position distal to the separated end of the first layer in a second clamp; inserting the separated end of the second layer into a slot of a spindle; turning the spindle and twisting the second layer around the spindle to separate the second layer from the first layer.

In another embodiment, further including the step of applying tension to the first layer prior to the step of turning.

In another embodiment, the step of applying tension is conducted by pulling the first clamp away from the second clamp.

In another embodiment, the first layer and the second layer are conjoined by a least one weld and the step of separating includes breaking the at least one weld.

In another embodiment, further including measuring the force required to separate the first layer from the second layer during the step of turning.

In another embodiment, further including the step of measuring bonding artifacts after the step of twisting.

In another embodiment, when the step of measuring is by image analysis.

In another embodiment, further including the step of straightening the member after the step of twisting and before the step of measuring.

BRIEF DESCRIPTION OF THE DRAWINGS

For a more complete understanding of the present disclosure, reference is made to the following detailed description of exemplary embodiments considered in conjunction with the accompanying drawings.

DETAILED DESCRIPTION OF EXEMPLARY EMBODIMENTS

Manual peel testing, which results in a highly distorted separated panels typically requires the artifacts of the joints thereof, e.g., spot weld "buttons" or holes to be measured by hand, e.g., with a set of calipers or micrometers. An aspect of the present disclosure is the recognition that peel testing of welded panels that yields a less distorted panel may allow the panels and welds to be analyzed automatically. In a similar vein, the present disclosure recognizes that straightening a distorted panel may facilitate automatic inspection. For example, a flat or flattened panel may be amenable to imaging and imaging analysis as disclosed in a U.S. patent application Ser. No. 14/702,204, filed May 1, 2015, entitled Apparatus and Methods for Weld Measurement, owned by the Assignee of the present application and incorporated in its entirety herein by reference. In another aspect of the present disclosure, the peel apparatus and method thereof may yield more consistent results than conventional methods and saves significant manual labor.

Figure 1:
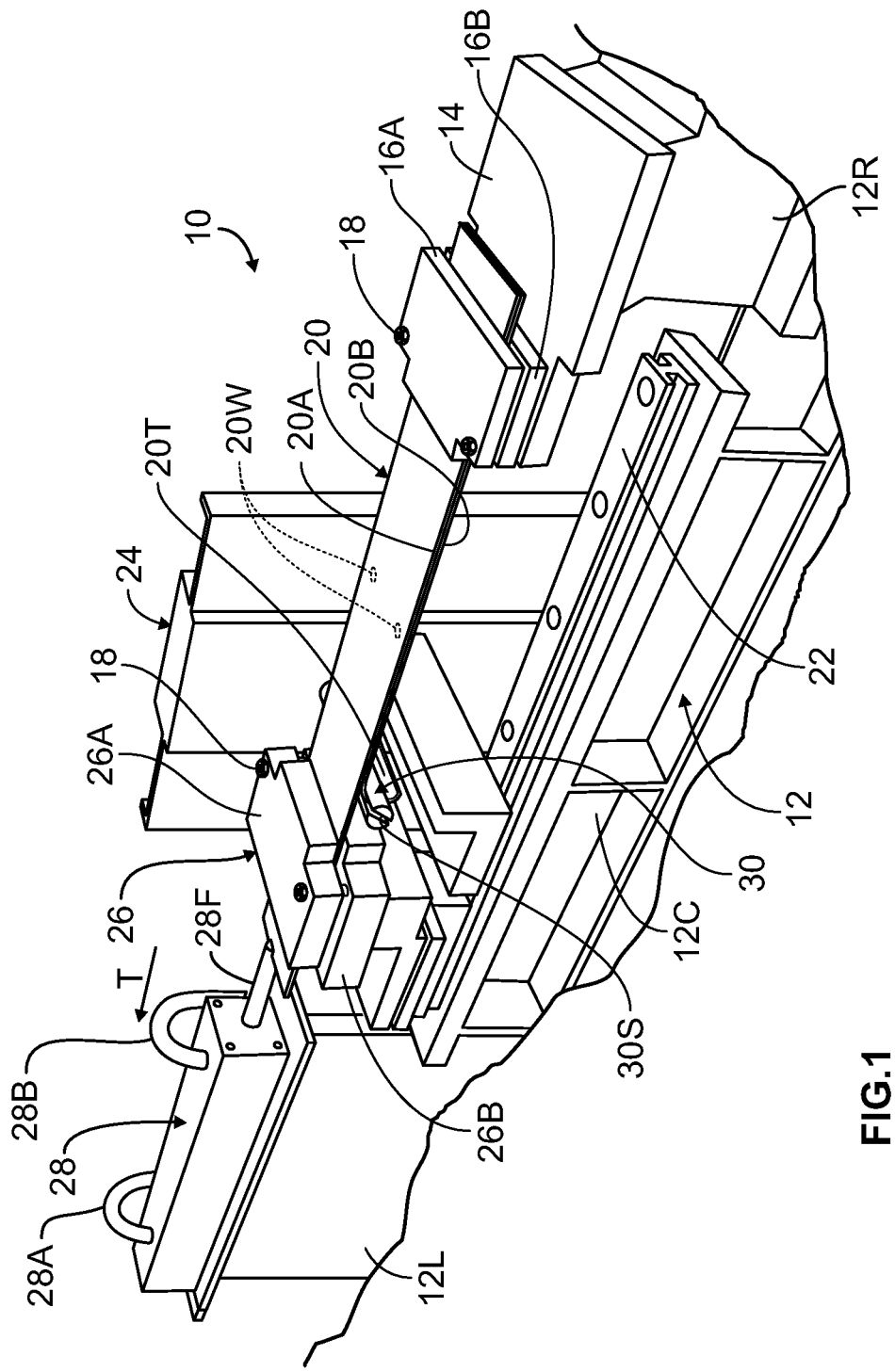
FIG. 1 is front perspective view of a peeling tool in accordance with an embodiment of the present disclosure.

FIG. 1 shows a peeling tool 10 with a base frame 12 having a center portion 12C and left and right portions 12L and 12R. The right portion 12R supports a right clamping platform 14 to which one or more clamp plates 16A, 16B may be attached by one or more bolts 18. A laminate sample 20 having layers 20A, 20B conjoined by welding, e.g., spot welds 20W (two of which are diagrammatically shown in dotted lines—any number or pattern being possible), may be inserted between the clamp plates 16A, 16B (or between a clamp plate 16A and the right clamping platform 14) at one end thereof and the bolts 18 tightened to firmly hold the sample 20 in association with the clamping platform 14 attached to the right portion 12R of the frame 12. While a threaded clamping mechanism is shown, a hydraulic or pneumatic cylinder could be used to exert clamping force on the sample 20 at the clamping platform 14. The frame 12 may be made of cast iron or fabricated of steel plate or another strong material capable of withstanding the forces generated by the peeling tool 10. The center portion 12C of the frame 12 supports a slide way 22 upon which a peeler 24 and a movable clamping platform 26 independently slide. The movable clamping platform 26 supports one or more clamp plates 28A, 28B that may be secured to the movable clamping platform 26 by bolts 18 that clamp the other (left) end of the sample 20 onto the movable clamping platform 26. As with clamping platform 14, hydraulic or pneumatic clamping mechanisms may be used at movable clamping platform 26. The left portion 12L of the frame 12 supports a hydraulic cylinder 28 with a piston rod 28P that attaches to the movable clamping platform 26, e.g., via a through pin. The hydraulic cylinder may be actuated by pressurized hydraulic fluid supplied/withdrawn by hydraulic lines 28A, 28B to pull the piston rod 28P and the coupled movable clamping platform 26 along the slide way 22 in a tensioning direction T to apply tension to the sample 20, the other end of the sample 20 being clamped to the clamping platform 14 that is rigidly held to the frame 12. Prior to clamping the sample 20 to the movable clamping platform 26, a tab portion 20T of one of the layers 20B, i.e., the lower layer, is bent down at an angle relative to the remainder of the sample 20 and threaded into a slot 30S in spindle 30 of the peeler 24. As a result, only the upper layer 20A of the sample 20 is held in tension between the clamping platforms 14 and 26, the tab 20T of the lower layer 20B being inserted into the spindle slot 30S rather than being clamped to the movable clamping platform 26. The peeler 24 is capable, as described more fully below, of turning the spindle 30, such that tab portion 20T inserted into the slot 30S is rotated by the spindle 30 and causes the lower layer 20B to wind about the exterior of the spindle 30. As the spindle 30 progressively winds the lower layer 20B around the spindle 30, a greater length of the lower layer 20B is pulled away from the upper layer 20A. When a bonded area, e.g., a spot weld that conjoins the layers 20A, 20B is encountered, the pulling force exerted by the turning spindle 30 tears the bond apart, which may result in the weld material of the bond being retained on one, the other, or both of the separated layers 20A, 20B. One or both layers 20A, 20B and the artifacts of the destroyed bond/weld 20W, e.g., a weld "button," hole or depression, may then be examined for dimensions and properties.

Figure 2:
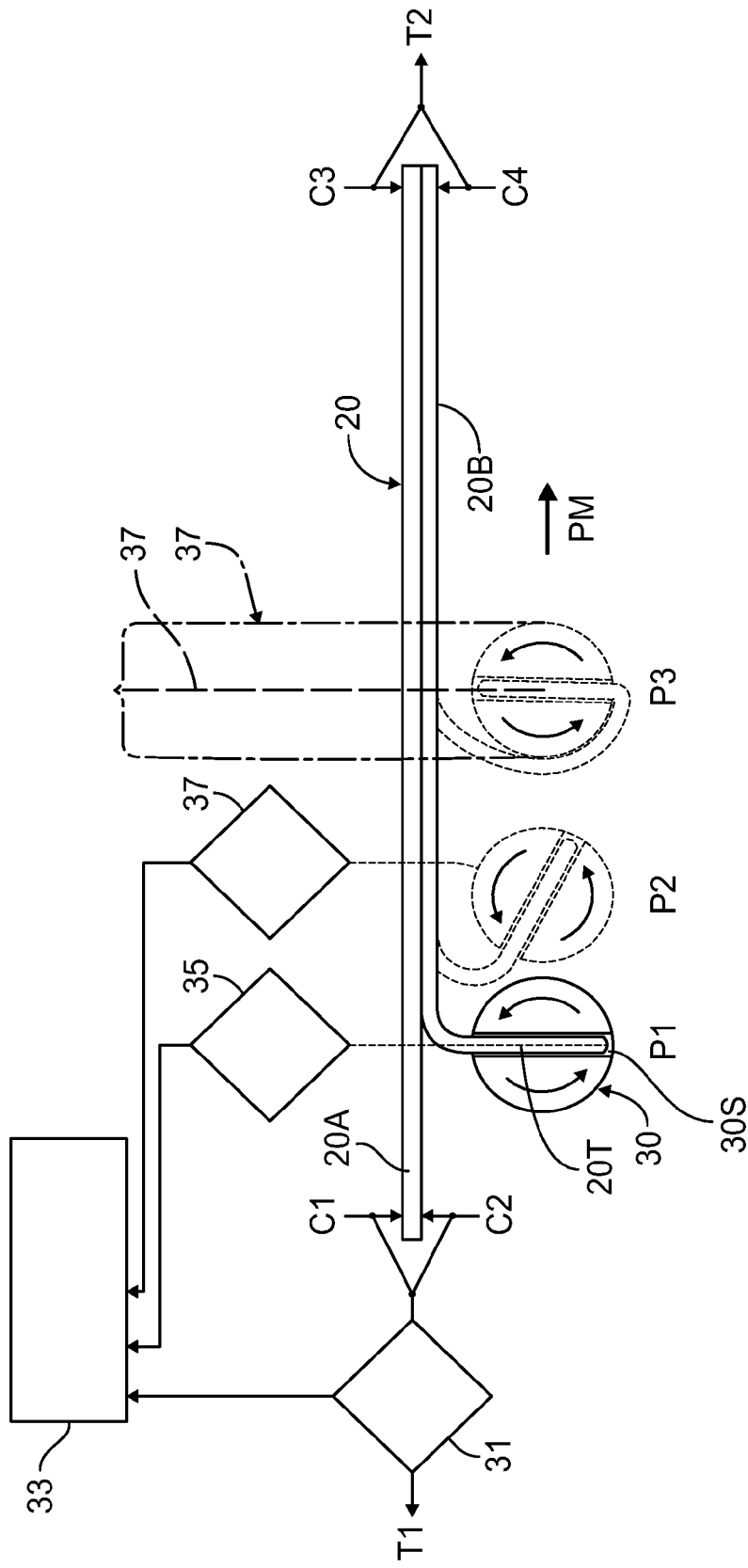
FIG. 2 is a diagrammatic view of a split spindle of the peeling tool of FIG. 1 in three stages of delaminating a pair of conjoined sheets.

FIG. 2 schematically depicts the peeling of the lower layer 20B from the upper layer 20A that is clamped at both ends by clamping forces C1, C2, C3, C4 and then pulled into tension by forces T1, T2. The tab portion 20T of the lower layer 20B is threaded into slot 30S at position P1. As the spindle 30 is rotated in the direction of the arrows, it progressively winds more of the layer 20B about itself, tearing/delaminating it from layer 20A. Because the peeler 24 is free to slide on slide way 22, as the spindle 30 rotates, winding and peeling layer 20B, the spindle 30 pulls peeler 24 along the slide way, e.g., to positions P2 and P3, as it tears the layer 20B from 20A. Layer 20A remains stretched between clamping platforms 14 and 26 until removed by releasing it from the clamping platforms 14 and 26. A transducer 31, such as a strain gauge positioned intermediate the hydraulic cylinder and the clamping platform 26, where it is subjected to tension force T1, may be monitored by a computer 33 or a data capture device, such that the forces encountered as the peeling tool 10 breaks the welds 20W or other joints bonding layers 20A, 20B may be recorded and analyzed. In another alternative, the transducer 31 may be a hydraulic pressure transducer communicating with the hydraulic fluid, e.g., in line 28B, that exerts the tensioning force T1 and therefore will reflect changing levels of tension T1 as the bonds between layers 20A, 20B are broken. In another alternative, a second or substitute transducer 35 sensing either mechanical strain exerted by the spindle 30 or force exerted by the motor 46 (see FIG. 4) that turns the spindle 30 may be employed to sense bond breaking force that is recorded and analyzed by computer 33. In the case of a hydraulic motor 46, the varying pressure encountered within the hydraulic motor or the hydraulic pressure line that moves it may be monitored over time by a hydraulic pressure sensor. An electric motor 46 may be monitored by a transducer 35 that measures the electric power used by the motor 46 as the layers 20A, 20B are separated. The position of the peeler 24 may also be sensed by a transducer 37 and the position recorded in computer 33. The force and position data recorded over time may be correlated to identify the force required to break a given weld 20W or set of welds 20W, which have a known position relative to the traversal path of the peeler 24. Alternatively, force peaks may be used to identify the force required to break welds 20W or sets thereof.

FIG. 2 also shows a simplified embodiment of the present disclosure. While the other embodiments illustrated utilize automated means for turning the spindle 30, a bar or handle 36 could be attached to the spindle 30 to provide a torque arm TA1 for turning the spindle 30, winding layer 20B and separating it from layer 20A. The bar 36 may be in the form of a crank to facilitate turning manually. In the case of a manually turned bar 36, the spindle 30 and bar 36 may or may not be mounted to the slide way 22, as further described below.

Figure 3:
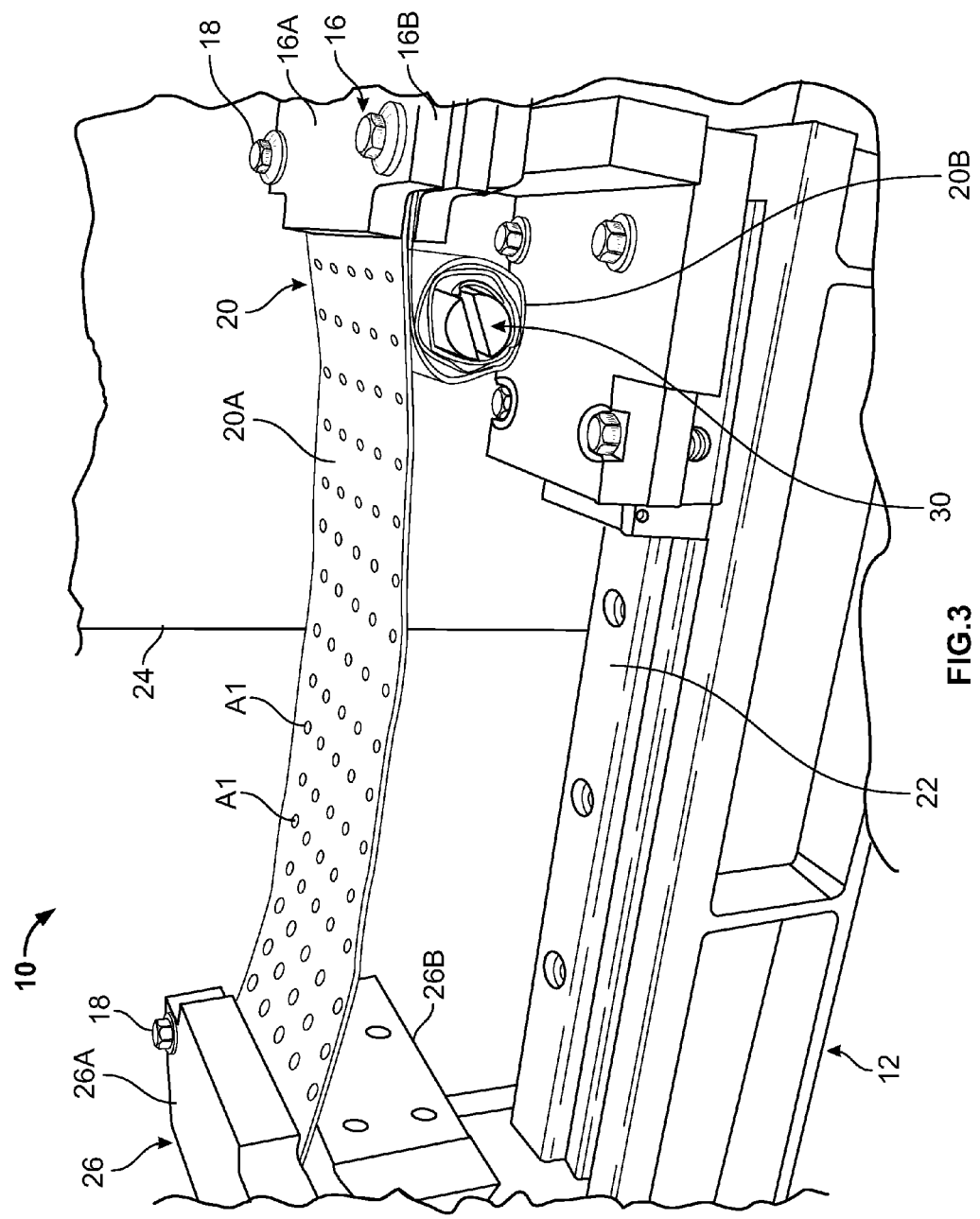
FIG. 3 is a front perspective view of the peeling tool of FIG. 1 as it approaches a state of completion of the peeling function.

FIG. 3 shows the peeling tool 10 as it approaches a state of completion of the peeling/delaminating function. More particularly, almost the entire lower layer 20B is wound around the spindle 30 of the peeler 24 breaking all welds 20W that previously conjoined the layers 20A, 20B. Artifacts A1 on the upper side of layer 20A can be observed at locations where each weld 20W previously existed. The artifacts, may be depressions where the weld 20W was pulled downwards by the peeler 24 or may be holes, depending upon the nature of the weld 20W and the way in which the specimen 20 was loaded into the peeling tool 10. In FIG. 3, the peeler 24 has pulled itself from its initial position proximate clamping platform 26 to stationary clamping platform 16, riding on slide 22. Once having reached a state of completing delamination of layer 20A and 20B, the layers 20A, 20B may be removed from the peeling tool 10 for inspection and analysis. FIG. 3 illustrates a condition in which the tension on the layer 20A has been relaxed, .i.e., by depressurizing hydraulic cylinder 28, allowing the sample 20 to be removed from the clamping platforms 14, 26 for examination.

Figure 4:
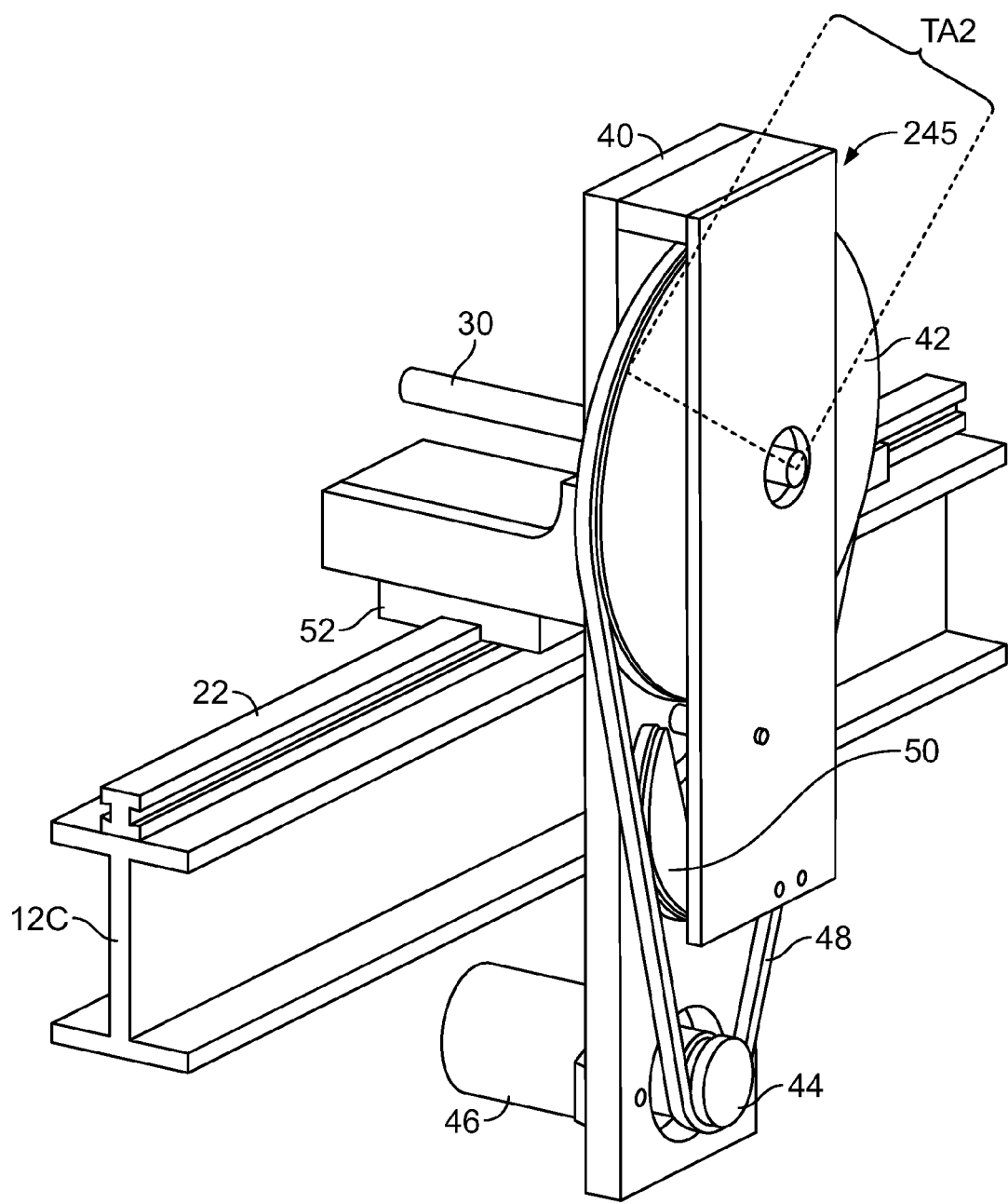
FIG. 4 is a rear perspective view of a peeler sub-assembly of the peeling tool of FIG. 1.

FIG. 4 shows is a rear perspective view of a peeler sub-assembly 24S of the peeling tool 10 of FIG. 1. The peeler subassembly has a housing 40 that rotatably supports a pulley 42 that drives spindle 30. The housing also supports a motor 46, e.g., a high torque electric or hydraulic motor that is bolted to the housing 40 via a flange (not shown). The motor 46 drives a pulley 44 aligned with pulley 42 via a belt 48 which extends there between, the radius of the pulley 42 providing a torque arm TA2 to facilitate rotation of the spindle 30. The pulleys 42, 44 may be in the form of sprockets and the belt 48 in the form of a drive chain. Alternatively, the pulleys 42, 44 could be replaced by intermeshing gears or a gear train that provides a suitable torque advantage between the motor 46 and the driven spindle 30. An idler 50 may be employed to maintain tension in the drive belt/chain 48. The housing 40 with attached motor 46, drive and driven pulleys 42, 44 and spindle 30 is attached to a tracking base 52 that rides on the slide way 22, e.g., on ball or roller bearings or simply a greased slot complementarily shaped to engage the slide way 22. One or the other of the pulleys 42, 44 may be coupled to a handle or crank that allows manually turning the spindle 30.

Figure 5:
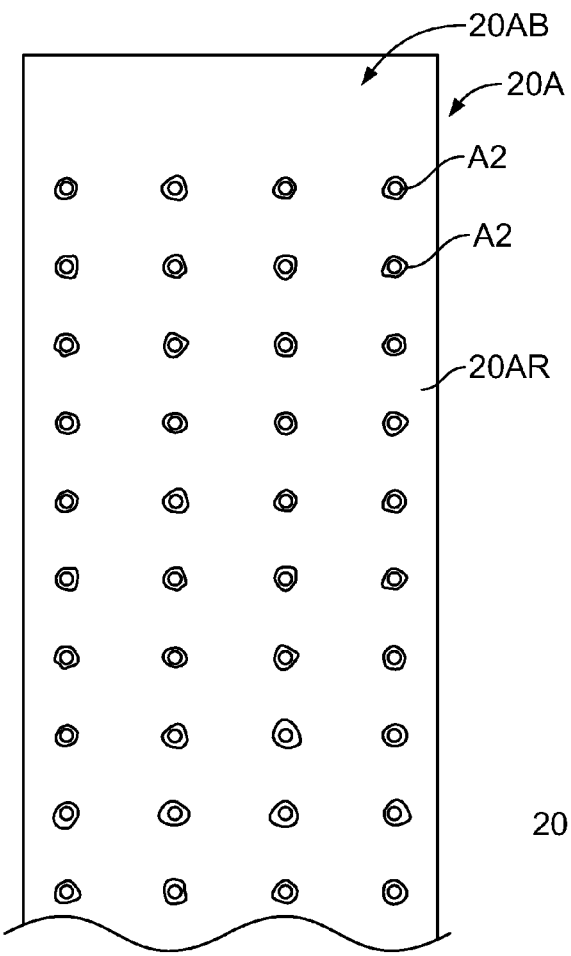
FIG. 5 is a perspective view of a first of a pair of conjoined sheets after delamination.

FIG. 5 shows a portion of the upper layer 20A after it has been delaminated from the specimen 20 and removed from the peeling tool 10. The bottom surface 20AB of the top layer 20A shows a plurality of artifacts A2, which may be raised weld "buttons" or depressed holes disposed on the remainder 20AR of the surface 20AB. These artifacts may be measured manually or automatically, e.g., as described in the application entitled, Apparatus and Methods for Weld Measurement which is incorporated herein by reference above. Because the upper layer 20A is stretched between the clamping platforms 14 and 16 under tension during peeling/delaminating, the delaminated layer 20A remains relatively straight during and after the peeling/delaminating process. This conformation of the delaminated layer 20A promotes ease of examination, either manually or automatically. In one alternative, the delaminated layer 20A may be further straightened, e.g., by pressing between the flat plates of a press or running it through a set of rollers. To avoid disturbing/deforming the artifacts A2, the rollers and or plates may be rubber or rubberized, or a rubber mat may be used to cover them when the delaminated layer 20A is flattened. Straightening the delaminated layer 20A into a generally planar configuration aids in automatic measurement/analysis, e.g., using vision systems and or image analysis.

Figure 6:
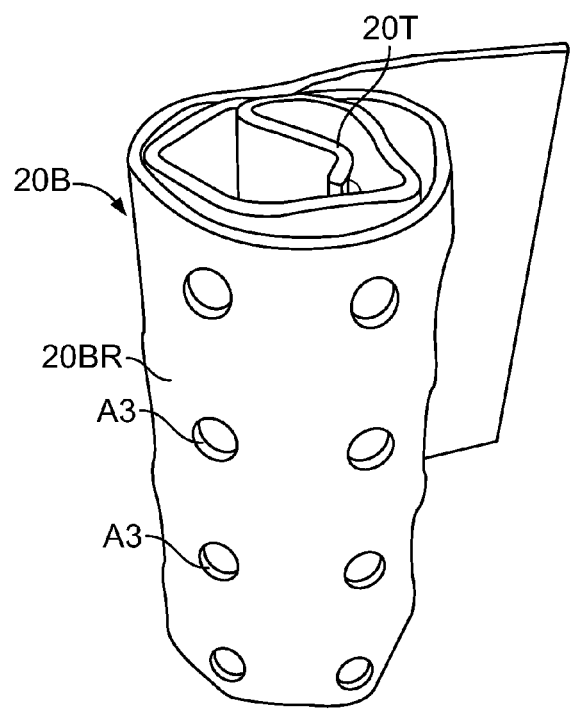
FIG. 6 is a perspective view of a second of a pair of conjoined sheets after delamination.

FIG. 6 shows the lower layer 20B after it has been delaminated by wrapping around the spindle 30. The tab portion 20T that is received in the slot 30S of the spindle 30 is disposed towards the center of the coiled lower layer 20B. A plurality of weld artifacts A3 are disposed over the remainder of the surface 20BR. If desired, the coiled lower layer 20B could be uncoiled and/or flattened for analysis/measurement of the artifacts A3.

It will be understood that the embodiments described herein are merely exemplary and that a person skilled in the art may make many variations and modifications without departing from the spirit and scope of the claimed subject matter. For example, while the present disclosure has referred to panels joined by resistance spot welds as examples, the same apparatus and methods may be used to separate panels joined by other welding processes such as fusion (GMAW, laser beam, examples, panels fastened by other methods, such as friction stir (spot, stitch, swing and friction bit joining), and mechanical fastening (self-pierce riveting, conventional riveting and use of threaded fasteners, clinching, flow drill screws, etc. or adherence by adhesives or solders). While the embodiments shown utilize clamping platforms 14, 26, using bolts for applying clamping pressure, a hydraulic, magnetic or pneumatically actuated clamp or a vice-like clamp could readily be employed. All such variations and modifications are intended to be included within the scope of the present disclosure.

We claim:

1. A device for separating a first layer from a second layer conjoined by at least one weld to form a member, comprising:
   a base structure;
   a first clamp mounted on the base structure capable of retaining a first portion of the member including the first layer and the second layer therein;
   a second clamp mounted on the base structure at a distance from the first clamp approximating at least a portion of a length of the member and capable of retaining a second portion of the member including the first layer therein;
   a rotatable spindle having a slot therein capable of receiving a portion of the second layer at a position intermediate the first clamp and the second clamp and twisting the first layer around the spindle when the spindle is rotated and while the first layer is clamped by the first clamp and the second clamp to break a weld of the at least one weld and separate the second layer from the first layer;
   a spindle mount rotatably supporting the spindle; and
   a spindle slide slidably supporting the spindle mount between a first position proximate the second clamp and a second position proximate the first clamp, the spindle mount free to slide along the spindle slide, whereby the twisting of the second layer around the spindle pulls the spindle and spindle mount along the slide towards the first clamp.

2. The device of claim 1, further comprising a member coupled to the spindle capable of applying torque to the spindle.

3. The device of claim 2, wherein the member is a pulley.

4. The device of claim 3, wherein the pulley is a sprocket.

5. The device of claim 3, wherein the pulley is a gear.

6. The device of claim 3, further comprising an engine capable of turning the pulley.

7. The device of claim 6, wherein the pulley is a first pulley and further comprising a second pulley coupled to the engine and a drive connection extending between the first pulley and the second pulley, the first and second pulleys and drive connection providing a torque advantage for the engine to turn the spindle.

8. The device of claim 2, wherein the member is a bar.

9. The device of claim 1, further comprising a transducer capable of measuring energy expended in separating the second layer from the first layer of the member.

10. The device of claim 1, further comprising a transducer capable of measuring force exerted by the spindle as the second layer is separated from the member for generating force data and further comprising a computer capable of receiving and storing the force data.

11. The device of claim 10, further comprising a transducer capable of sensing a position of the spindle relative to the member and generating position data, the computer capable of correlating the force data and the position data.

12. A device for separating a first layer from a second layer conjoined to form a member, comprising:
   a base structure;
   a first clamp mounted on the base structure capable of retaining a first portion of the member including the first layer and the second layer therein;
   a second clamp mounted on the base structure at a distance from the first clamp approximating at least a portion of a length of the member and capable of retaining a second portion of the member including the first layer therein;
   a rotatable spindle having a slot therein capable of receiving a portion of the second layer at a position intermediate the first clamp and the second clamp and twisting the second layer around the spindle when the spindle is rotated and while the first layer is clamped by the first clamp and the second clamp to separate the second layer from the first layer, wherein the second clamp is movable and further comprising a tensioner coupled to the second clamp and capable of applying tension to the member.

13. The device of claim 12, wherein the tensioner is hydraulically actuated.

14. The device of claim 12, further comprising a slide and wherein the second clamp is mounted on the slide and capable of sliding on the slide in response to the application of tension by the tensioner.

15. The device of claim 12, further comprising a transducer capable of measuring tension experienced by the member as the second layer is separated from the member.

16. A method for separating a first layer from a second layer conjoined by at least one weld to form a member, comprising:
   separating an end of the first layer from the second layer to form a separated end of the first layer and a separated end of the second layer;
   securing the separated end of the first layer in a first clamp;
   securing the member at a position distal to the separated end of the first layer in a second clamp;
   inserting the separated end of the second layer into a slot of a spindle rotatably supported in a spindle mount, the spindle mount slidably supported on a spindle slide between a first position proximate the first clamp and a second position proximate the second clamp;
   turning the spindle and twisting the second layer around the spindle to separate the second layer from the first layer breaking a weld of the at least one weld, the twisting of the second layer around the spindle causing the spindle and the spindle mount to be pulled towards the second clamp, and further causing the spindle mount to slide on the spindle slide.

17. The method of claim 16, wherein the first layer and the second layer are conjoined by a least one weld and the step of separating includes breaking the at least one weld.

18. The method of claim 16, further comprising measuring the force required to separate the first layer from the second layer during the step of turning.

19. The method of claim 16, further comprising the step of measuring at least one dimension of bonding artifacts after the step of twisting.

20. The method of claim 19, when the step of measuring is by image analysis.

21. The method of claim 20, further comprising the step of straightening the second member to a planar configuration after the step of twisting and before the step of measuring.

22. A method for separating a first layer from a second layer conjoined to form a member, comprising:
   separating an end of the first layer from the second layer to form a separated end of the first layer and a separated end of the second layer;
   securing the separated end of the first layer in a first clamp;
   securing the member at a position distal to the separated end of the first layer in a second clamp;
   inserting the separated end of the second layer into a slot of a spindle;
   applying tension to the first layer;
   turning the spindle and twisting the second layer around the spindle to separate the second layer from the first layer.

23. The method of claim 22, wherein the step of applying tension is conducted by pulling the first clamp away from the second clamp.

* * * * *